United States Patent
Katnani et al.

(10) Patent No.: US 11,602,296 B2
(45) Date of Patent: *Mar. 14, 2023

(54) NON-INVASIVE SYSTEMS AND METHODS FOR DETECTING MENTAL IMPAIRMENT

(71) Applicant: HI LLC, Los Angeles, CA (US)

(72) Inventors: Husam Katnani, Braintree, MA (US); Daniel Sobek, Portola Valley, CA (US); Antonio H. Lara, Sherman Oaks, CA (US)

(73) Assignee: HI LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/586,249

(22) Filed: Jan. 27, 2022

(65) Prior Publication Data
US 2022/0142536 A1    May 12, 2022

Related U.S. Application Data

(63) Continuation of application No. 16/523,861, filed on Jul. 26, 2019, now Pat. No. 11,272,870.

(Continued)

(51) Int. Cl.
*G08B 23/00*  (2006.01)
*A61B 5/16*  (2006.01)
(Continued)

(52) U.S. Cl.
CPC .............. *A61B 5/165* (2013.01); *A61B 5/162* (2013.01); *A61B 5/18* (2013.01); *A61B 5/377* (2021.01);
(Continued)

(58) Field of Classification Search
CPC ..... A61B 3/113; A61B 5/0022; A61B 5/0059; A61B 5/04009; A61B 5/0478;
(Continued)

(56) References Cited

U.S. PATENT DOCUMENTS

| 5,377,100 A | 12/1994 | Pope et al. |
| 5,720,619 A | 2/1998 | Fisslinger |

(Continued)

FOREIGN PATENT DOCUMENTS

| EP | 2939706 | 11/2015 |
| WO | WO02043564 | 6/2002 |

(Continued)

OTHER PUBLICATIONS

Lee, B.T., Seok, J.H., Lee., B.C, Cho, S.W., Chai, J.H., Choi, I.G., Ham, B.J., "Neural correlates of affective processing in response to sad and angry facial stimuli in patients with major depressive disorder," Prog Neuropsychopharmacol Biol Psychiatry, 32(3), 778-85 (2008).

(Continued)

*Primary Examiner* — Naomi J Small
(74) *Attorney, Agent, or Firm* — Michael J. Bolan; Vista IP Law Group LLP

(57) ABSTRACT

A mental impairment detection system and non-invasive method of detecting mental impairment of a user are provided. A test (e.g., an inhibitory reflex test or a sustained attention test) is administered to the user, brain activity in a frontal lobe of the user is non-invasively detected while the test is administered to the user, and a level of mental impairment of the user is determined based on the brain activity detected in the frontal lobe of the user.

27 Claims, 9 Drawing Sheets

Related U.S. Application Data

(60) Provisional application No. 62/712,141, filed on Jul. 30, 2018.

(51) Int. Cl.
| | |
|---|---|
| *A61B 5/18* | (2006.01) |
| *A61B 5/00* | (2006.01) |
| *A61B 5/377* | (2021.01) |
| *A61B 3/113* | (2006.01) |
| *A61B 5/291* | (2021.01) |

(52) U.S. Cl.
CPC .......... *A61B 5/4064* (2013.01); *A61B 5/6803* (2013.01); *A61B 3/113* (2013.01); *A61B 5/168* (2013.01); *A61B 5/291* (2021.01); *A61B 5/4023* (2013.01); *A61B 5/7257* (2013.01); *A61B 5/7275* (2013.01)

(58) Field of Classification Search
CPC ..... A61B 5/0484; A61B 5/1114; A61B 5/162; A61B 5/163; A61B 5/165; A61B 5/168; A61B 5/18; A61B 5/4023; A61B 5/4064; A61B 5/6803; A61B 5/7257; A61B 5/7275; G09B 7/00
USPC ....................................................... 340/573.1
See application file for complete search history.

(56) References Cited

U.S. PATENT DOCUMENTS

| | | | |
|---|---|---|---|
| 5,853,370 A | 12/1998 | Chance et al. | |
| 6,231,187 B1* | 5/2001 | Munoz ................... | A61B 3/113 351/209 |
| 6,488,617 B1 | 12/2002 | Katz | |
| 8,473,024 B2 | 6/2013 | Causevic et al. | |
| 8,609,162 B2 | 12/2013 | Giuliano et al. | |
| 9,101,279 B2 | 8/2015 | Ritchey et al. | |
| 9,114,140 B2 | 8/2015 | Giuliano et al. | |
| 9,265,974 B2 | 2/2016 | You et al. | |
| 9,339,227 B2 | 5/2016 | Darcy et al. | |
| 9,417,106 B2 | 8/2016 | Tobita | |
| 9,440,064 B2 | 9/2016 | Wingeier et al. | |
| 9,712,736 B2 | 7/2017 | Kearns et al. | |
| 9,729,252 B2 | 8/2017 | Tyler et al. | |
| 9,943,698 B2 | 4/2018 | Chase et al. | |
| 9,946,344 B2 | 4/2018 | Ayaz et al. | |
| D817,553 S | 5/2018 | Aaskov et al. | |
| D825,112 S | 8/2018 | Saez | |
| 10,091,554 B1 | 10/2018 | Newell et al. | |
| 10,188,860 B2 | 1/2019 | Wingeier et al. | |
| 10,234,942 B2 | 3/2019 | Connor | |
| 10,258,760 B1 | 4/2019 | Sherpa et al. | |
| 2003/0176806 A1 | 9/2003 | Pineda et al. | |
| 2004/0049134 A1 | 3/2004 | Tosaya et al. | |
| 2005/0273017 A1* | 12/2005 | Gordon ................ | A61B 5/4088 600/544 |
| 2006/0150989 A1 | 7/2006 | Migaly | |
| 2006/0161218 A1 | 7/2006 | Danilov | |
| 2008/0177197 A1 | 7/2008 | Lee et al. | |
| 2012/0172743 A1 | 7/2012 | Aguilar et al. | |
| 2013/0211238 A1 | 8/2013 | DeCharms | |
| 2013/0289385 A1 | 10/2013 | Lozano et al. | |
| 2013/0311132 A1 | 11/2013 | Tobita | |
| 2014/0023999 A1 | 1/2014 | Greder | |
| 2014/0200432 A1 | 7/2014 | Banerji et al. | |
| 2014/0228701 A1 | 8/2014 | Chizeck et al. | |
| 2014/0303450 A1 | 10/2014 | Caponi | |
| 2014/0347265 A1 | 11/2014 | Aimone et al. | |
| 2015/0092056 A1* | 4/2015 | Rau ........................ | B60R 11/04 348/148 |
| 2015/0290454 A1 | 10/2015 | Tyler et al. | |
| 2015/0297109 A1 | 10/2015 | Garten | |
| 2015/0355462 A1 | 12/2015 | Saito et al. | |
| 2016/0077547 A1* | 3/2016 | Aimone ................ | A61B 5/1114 345/8 |
| 2016/0220163 A1 | 8/2016 | Yamada | |
| 2016/0242690 A1 | 8/2016 | Principe et al. | |
| 2016/0270656 A1 | 9/2016 | Samec et al. | |
| 2016/0349274 A1* | 12/2016 | Williams ........... | G01N 33/6896 |
| 2017/0042439 A1 | 2/2017 | Yeow | |
| 2017/0202518 A1 | 7/2017 | Furman et al. | |
| 2017/0229037 A1 | 8/2017 | Gazzaley | |
| 2017/0323485 A1* | 11/2017 | Samec ................ | A61B 5/14532 |
| 2017/0347906 A1* | 12/2017 | Intrator ................ | A61B 5/7264 |
| 2017/0352283 A1 | 12/2017 | Lau | |
| 2018/0092557 A1 | 4/2018 | Bickford et al. | |
| 2018/0278984 A1 | 9/2018 | Aimone | |
| 2018/0299953 A1* | 10/2018 | Selker ................... | G06F 3/0346 |
| 2018/0348863 A1 | 12/2018 | Aimone et al. | |
| 2019/0021657 A1 | 1/2019 | Mohammadrezazadeh et al. | |
| 2019/0082990 A1 | 3/2019 | Poltorak | |
| 2019/0200888 A1 | 7/2019 | Poltorak | |
| 2019/0201691 A1 | 7/2019 | Poltorak | |
| 2019/0224441 A1 | 7/2019 | Poltorak | |
| 2019/0246929 A1 | 8/2019 | Poltorak | |
| 2019/0247662 A1 | 8/2019 | Poltorak | |
| 2019/0321583 A1 | 10/2019 | Poltorak | |

FOREIGN PATENT DOCUMENTS

| | | | |
|---|---|---|---|
| WO | WO2012135068 | 10/2012 | |
| WO | WO2014055932 | 4/2014 | |
| WO | WO2016022414 | 2/2016 | |
| WO | WO-2016022414 A1 * | 2/2016 | ............. A61B 3/113 |
| WO | WO2019104008 | 5/2019 | |

OTHER PUBLICATIONS

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50, 414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision-making in the human brain," Nature, 431, 859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10),1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

Sheline YI, Price JL, Yan Z, Mintun MA, "Resting-state functional MRI in depression unmasks increased connectivity between networks via the dorsal nexus," Proc Natl Acad Sci., 107(24), 11020-11025 (2010).

Bari A, Robbins TW, "Inhibition and impulsivity: Behavioral and neural basis of response control," Prog Neurobiol., 108:44-79 (2013).

(56) References Cited

OTHER PUBLICATIONS

Kagias, Konstantinos et al. "Neuronal responses to physiological stress," Frontiers in genetics, 3:222 (2012).
Clark, Ian A., et al., "First steps in using machine learning on fMRI data to predict intrusive memories of traumatic film footage", 0005-7967/ 2014 The Authors. Published by Elsevier Ltd. Behaviour Research and Therapy. This is an open access article under the CC by license (http://creativecommons.org/licenses/by/3.0/); 10 pgs.
George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.
Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.
S.Z.K, Tan et al. ."Eternal sunshine of the neuromodulated mind: Altering fear memories through neuromodulation", Experimental Neurology 314 (2019) 9-19, 11 pages.
Zhang, Fei-Fei, et al., "Brain structure alterations in depression: Psychoradiological evidence", CNS Neurosci T 2018, John Wiley & Sons Ltd her. 2018;24:994-1003, 10 pages.
Non-Final Office Action received in U.S. Appl. No. 16/364,338, dated Oct. 4, 2019.
Amendment and response filed in U.S. Appl. No. 16/364,338, dated Nov. 8, 2019.
Final Office Action received in U.S. Appl. No. 16/364,338, dated Jan. 27, 2020.
Amendment and response filed in U.S. Appl. No. 16/364,338 dated Feb. 26, 2020.
Non-Final Office Action received in U.S. Appl. No. 16/364,338 dated Mar. 23, 2020.
PCT International Search Report and Written Opinion for International Appln. No. PCT/US2019/043768, Applicant HI LLC, forms PCT/ISA/210, 220 and 237 dated Oct. 15, 2019 (11 pages).
Marianna Papadopoulou et al.; "Event-related potentials before saccades and antisaccades and their relation to reaction time", Experimental Brain Research, Springer, Berlin, DE, vol. 205, No. 4, Aug. 14, 2010, pp. 521-531, XP019840052.
Frank Schmal et al., "Effect of Ethanol on Visual-Vestibular Interactions During Vertical Linear Body Acceleration", Alcoholism: Clinical and Experimental Research, vol. 27, No. 9, Sep. 1, 2003, pp. 1520-1526, XP055626675.
Stefan K. Ehrlich, et al., "A closed-loop, music-based brain-computer interface for emotion mediation",PLoS One 14(3): e0213516. https://doi.org/10.1371/journal.pone.0213516; Mar. 18, 2019.
Patrick Gomez, et al., "Relationships Between Musical Structure and Psychophysiological Measures of Emotion", American Psychological Association, vol. 7, No. 2, 2007, pp. 377-387, (10 pages).
Fernando Lopes da Silva, "EEG and MEG: Relevance to Neuroscience", Center of Neuroscience; http://dx.doi.org/10.1016/j.neuron.2013.10.017; (17 pages).
Elena Boto, et al., "A new generation of magnetoencephalography: Room temperature measurements using optically-pumped magnetometers", NeuroImage 149 (2017)404-414; (11 pages).
Stanislas Dehaene, et al., "Imaging unconscious semantic priming", Nature; vol. 395; Oct. 8, 1998; (4 pages).
John D. E. Gabrieli, et al., "The role of left prefrontal cortex in language and memory", Proc. Natl. Acad. Sci. USA, vol. 95, pp. 906-913, Feb. 1998; (8 pages).
Yang Jiang, et al., "Turning Upthe Old Brain with New Tricks: Attention Training via Neurofeedback", Frontiers in Aging Neuroscience; Mar. 2017; vol. 9; Article 52; (9 pages).
Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; (3 pages).
Samat Moldakarimova, et al., "Perceptual priming leads to reduction of gamma frequency oscillations", PNAS, Mar. 23, 2010, vol. 107, No. 12; (6 pages).
M. Teplan, "Fundamentals of EEG Measurement", Measurement Science Review, vol. 2, Section 2, 2002; (11 pages).
Judith Amores, et al., "Promoting Relaxation Using Virtual Reality, Olfactory Interfaces and Wearable EEG," 2018 IEEE 15th International Conference on Waerable and Implantable Body Sensor Networks; Mar. 4, 2018, (4 pages).
PCT International Search Report and Written Opinion for International Appln. No. PCT/US2020/029031, Applicant HI LLC, forms PCT/ISA/210, 220 and 237 dated Sep. 2, 2020 (18 pages).
Final Office Action received in U.S. Appl. No. 16/364,338 dated Jul. 29, 2020.
PCT International Search Report and Written Opinion for International Appln. No. PCT/US2020/025971, Applicant HI LLC, forms PCT/ISA/210, 220 and 237 dated Sep. 15, 2020 (15 pages).
PCT International Search Report and Written Opinion for International Appln. No. PCT/US2020/034831, Applicant HI LLC, forms PCT/ISA/210 and 237 dated Feb. 8, 2021 (18 pages).
PCT International Search Report and Written Opinion for International Appln. No. PCT/US2019/024027, Applicant HI LLC, forms PCT/ISA/210, 220 and 237 dated Aug. 19, 2019 (13 pages).

\* cited by examiner

NON-INVASIVE SYSTEMS AND METHODS FOR DETECTING MENTAL IMPAIRMENT

RELATED APPLICATION DATA

The present application is a continuation of U.S. patent application Ser. No. 16/523,861, filed Jul. 26, 2019, which claims the benefit of U.S. Provisional Patent Application Ser. No. 62/712,141, filed Jul. 30, 2018, which are expressly incorporated herein by reference.

FIELD OF THE INVENTION

The present inventions relate to methods and systems for non-invasive measurements in the human body, and in particular, methods and systems related to detecting mental impairment.

BACKGROUND OF THE INVENTION

The operation of transportation vehicles, such as cars, motorcycles, trucks, and airplanes, as well as the performance of high responsibility jobs, such as air traffic controllers and heavy machinery operators (e.g., a forklift or crane), by individuals who are temporarily mentally impaired due to the influence of chemical substances, such as drugs (prescription or recreational) and alcohol, sleep deprivation, or brain injury (e.g., stroke or concussion) is a major problem. Not only do such mentally impaired persons put their own lives at risk, they put innocent lives at risk as well. In addition to putting lives at risk, such mentally impaired individuals are subject to fines, license revocation or suspension, firing or suspension from employment, and criminal prosecution.

In many cases, individuals that are temporarily mentally impaired are not aware or are unsure of the extent of their mental impairment. There exists sobriety screening or monitoring systems that allow an individual to measure his or her own alcohol blood level, thereby providing such individual an indication of the extent of mental impairment due to alcohol consumption. However, such systems only measure the level of alcohol content, and do not actually measure the level of impairment, of the individual being tested, and thus, may not accurately determine the ability of the individual to operate transportation vehicles or perform high responsibility jobs. For example, alcohol tolerance levels may vary greatly amongst individuals, and more importantly, individuals with low alcohol tolerance levels may actually be mentally impaired to the extent that operating transportation vehicles or performing high responsibility jobs would be considered unsafe despite the fact the blood alcohol level of such individuals may indicate that they are not so impaired. Furthermore, such sobriety screening systems do not take into account non-alcoholic causes of temporary mental impairment or other various levels of mental impairment, such as prescription or recreational drugs, as well as pre-existing medical conditions caused by disease or injury that may mentally impair an individual that is not under the influence of alcohol.

There, thus, remains a need to determine the level that an individual is actually impaired with respect to operating transportation vehicles or performing high responsibility jobs.

SUMMARY OF THE INVENTION

In accordance with one aspect of the present inventions, a mental impairment detection system comprises a sensory stimulation device (e.g., a display device) configured for administering a test to a user that evokes a process in a frontal lobe (e.g., in a premotor cortex or dorsolateral prefrontal cortex) of the user, a non-invasive brain interface assembly configured for detecting brain activity in the frontal lobe of the user while the test is administered to the user, and at least one processor configured for determining a level of mental impairment of the user based on the brain activity detected in the frontal lobe of the user. In one embodiment, the mental impairment detection system further comprises a communication device (e.g., at least one speaker) configured for instructing the user how to perform the test.

In one embodiment, the processor(s) is configured for determining the level of mental impairment of the user by quantifying results of the test administered to the user based on the brain activity detected in the frontal lobe of the user, e.g., by further comparing the quantified results of the test administered to the user to baseline quantified results of the test administered to the user when the user is known to not be mentally impaired. In another embodiment, the mental impairment detection system further comprises a camera configured for tracking head movements of the user, wherein the at least one processor is configured for determining the level of impairment of the user further based on the tracked head movements of the user. In still another embodiment, the sensor stimulation device is further configured for administering a reflex test to the user, in which case, the non-invasive brain interface assembly may be further configured for detecting brain activity in a non-frontal lobe of the user while the reflex test is administered to the user, and the processor(s) may be configured for determining the level of impairment of the user further based on the brain activity detected in the non-frontal lobe of the user. The non-invasive brain interface assembly may, e.g., one of an optical measurement assembly and a magnetic measurement assembly, and may, e.g., comprise at least one sensor configured for detecting energy from a brain of the user, and processing circuitry configured for identifying the brain activity in response to detecting the energy from the brain of the user. The non-invasive brain interface assembly may comprise, e.g., a head-worn unit carrying the sensor(s), and a computer containing the processor(s).

In accordance with another aspect of the present inventions, a non-invasive method of detecting mental impairment of a user comprises administering a test to the user (e.g., via displaying) that evokes a process in a frontal lobe (e.g., in a premotor cortex or dorsolateral prefrontal cortex) of the user, non-invasively detecting brain activity in the frontal lobe of the user (e.g., optically detecting the brain activity of the user and magnetically detecting the brain activity of the user) while the test is administered to the user, and determining a level of mental impairment of the user based on the brain activity detected in the frontal lobe of the user. The method may further comprise instructing the user how to take the test.

In one method, determining the level of mental impairment of the user comprises quantifying results of the test administered to the user based on the brain activity detected in the frontal lobe of the user, e.g., by further comparing the quantified results of the test administered to the user to baseline quantified results of the test administered to the user when the user is known to not be mentally impaired. Another method further comprises tracking head movements of the user, wherein the level of impairment of the user is further based on the tracked head movements of the user. Still another method further comprises administering a reflex test to the user, and detecting brain activity in a non-frontal lobe of the user while the reflex test is administered to the user. In this case, the level of impairment of the user may be determined further based on the brain activity detected in the non-frontal lobe of the user.

The test administered to the user may be an inhibitory reflex test. In one embodiment, the inhibitory reflex test comprises an anti-saccade task. In this case, displaying the inhibitory reflex test may comprise displaying a motionless target in a center of a field of vision of the user, and subsequently displaying a first visual stimulus in a periphery of the field of vision of the user. The user may be instructed to fixate on the motionless target, and to make a saccade in a direction away from the first visual stimulus when the first visual stimulus is displayed in the periphery of the field of vision of the user. The inhibitory reflex test may further comprise a saccade task. In this case, displaying the inhibitory reflex test further comprises randomly or pseudo-randomly displaying the first visual stimulus or a second visual stimulus different from the first visual stimulus one at a time in the periphery of the field of the vision of the user, in which case, the user may be instructed to make a saccade in a direction towards the second visual stimulus when the second visual stimulus is displayed in the periphery of the field of vision of the user. The level of impairment of the user may be determined by determining either a reaction time or an error of the user in response to the anti-saccade task. In another embodiment, the inhibitory reflex test comprises go/no-go tasks.

Alternatively, the test administered to the user may be a sustained attention test to the user comprises displaying the sustained attention test to the user. In one embodiment, the sustained attention test comprises a psychomotor vigilance task. In this case, displaying the sustained attention test may comprise randomly or pseudo-randomly presenting a visual stimulus every few seconds over a period of time. The communication device may be configured for instructing the user to perform an action in response to each stimulus. In another embodiment, the sustained attention test comprises go/no-go tasks. In this case, displaying the sustained attention test may comprise randomly or pseudo-randomly presenting different types of stimuli one-at-a-time. In another embodiment, the inhibitory reflex test comprises go/no-go tasks. In this case, displaying the sustained attention test may comprise randomly or pseudo-randomly presenting different types of stimuli one-at-a-time. The user may be instructed to perform an action if one type of stimulus is presented to the user, and to not perform the action if another different type of stimulus is presented to the user.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The non-invasive impairment detection system described herein is capable of determining a level of mental impairment of an individual by measuring the executive response inhibition of that individual to a stimulus. When functioning properly, the executive response inhibition rapidly cancels motor activity even after its initiation, and thus, is significantly impacted by mental impairment of that individual. In contrast to a reflexive response (e.g., patellar reflex), which involves a bottom-up mechanism in the body that does not engage the executive brain function of an individual, and thus is not significantly impacted by mental impairment of that individual, the non-invasive impairment detection system described herein focuses on an inhibitory reflex response, which involves a top-down mechanism in the body that does engage the executive brain function of the individual. As such, it is believed that measuring the inhibitory reflex response of an individual provides a good indication of whether or not the top-down mechanism of the individual is properly operating, thereby providing a robust and accurate means of measuring the mental impairment of the individual under a variety of different conditions, including the influence of chemical substances, such as drugs (prescription or recreational) and alcohol, sleep deprivation, or brain injury (e.g., stroke or concussion).

To this end, the non-invasive impairment detection system described herein presents an inhibitory reflex test to a user, non-invasively detects brain activity in the frontal lobe of the user while the user performs the inhibitory reflex test, and determines the level of mental impairment of the user based on the brain activity detected in the frontal lobe of the user.

Figure 1:
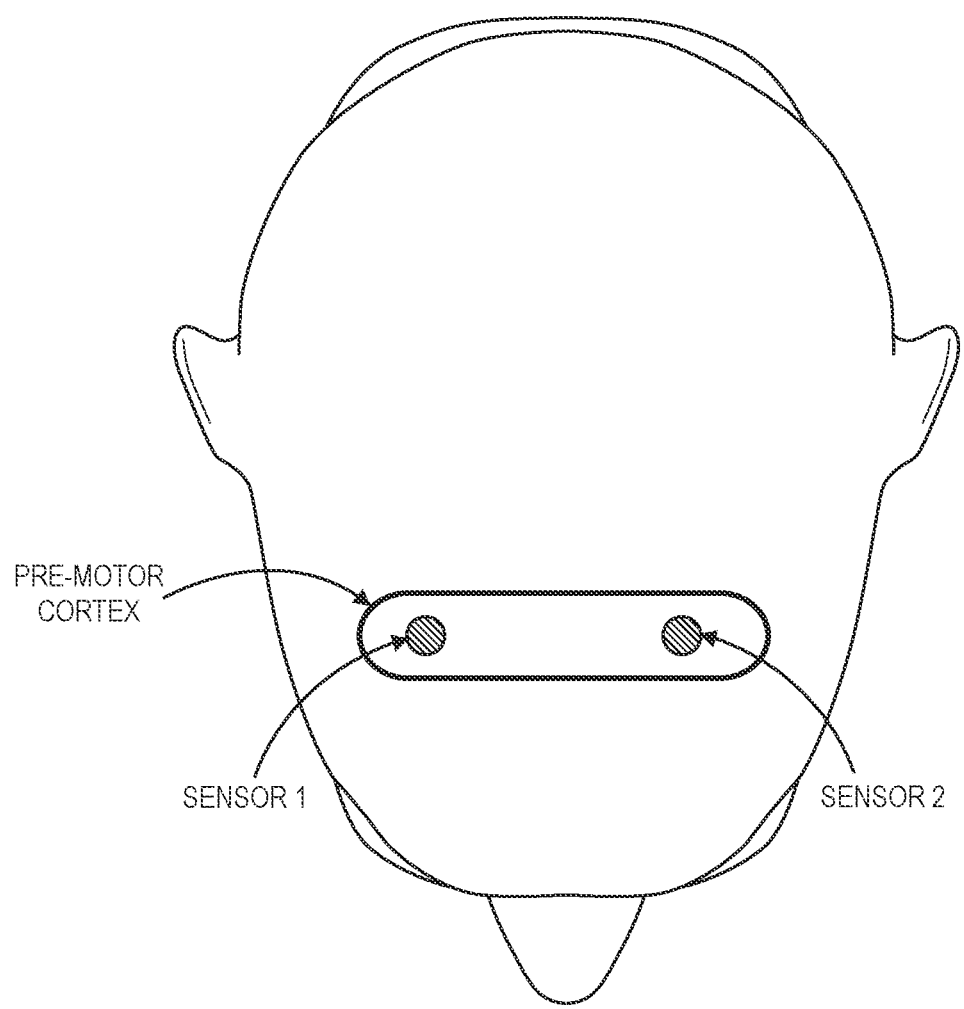
FIG. 1 is a top view of a head of a person, particularly illustrating sensors used by a non-invasive mental impairment detection system constructed in accordance with one embodiment of the present inventions to detect brain activity from the pre-motor cortex of a user.

In the preferred embodiment of the non-invasive impairment detection system, the brain activity of the premotor cortex in the frontal lobe of the user is bilaterally measured (e.g., with sensor 1 and sensor 2), as illustrated in FIG. 1. The premotor cortex is an area of the motor cortex within the frontal lobe of the brain just anterior to the primary motor cortex (top front of the head), and is believed to play a role in planning sensory guided movement that is subsequently executed by the primary motor cortex. Different sub-regions of the premotor cortex have different properties and presumably emphasize different functions. The brain signals generated in the premotor cortex cause much more complex patterns of movement than the discrete patterns generated in the primary motor cortex.

Figure 2A:
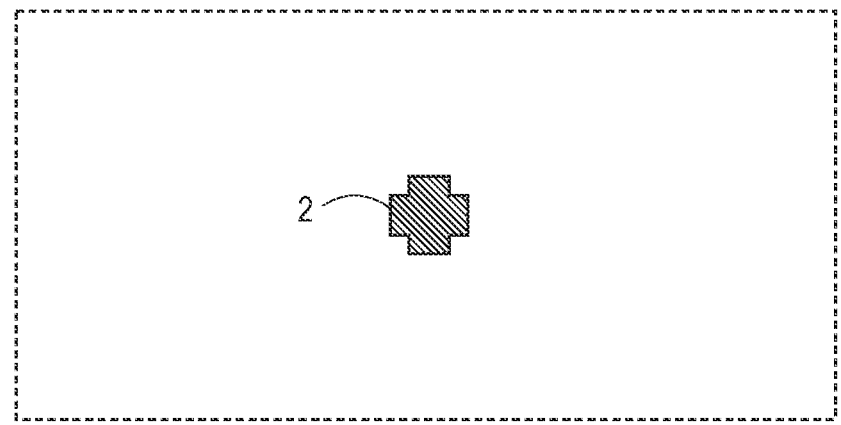
FIG. 2A is a diagram illustrating an inhibitory reflex text administered to a user by the mental impairment detection system, particularly showing a motionless target on which the user fixates.
Figure 2B:
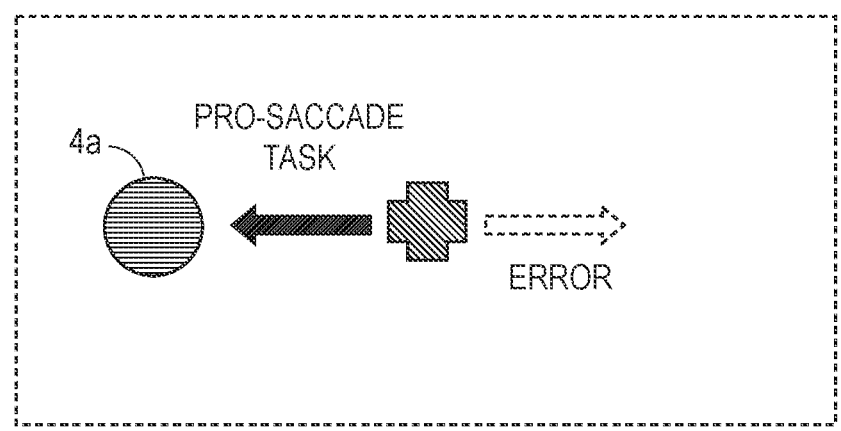
FIG. 2B is a diagram illustrating an inhibitory reflex text administered to a user by the mental impairment detection system, particularly showing a pro-saccade task performed by the user.
Figure 2C:
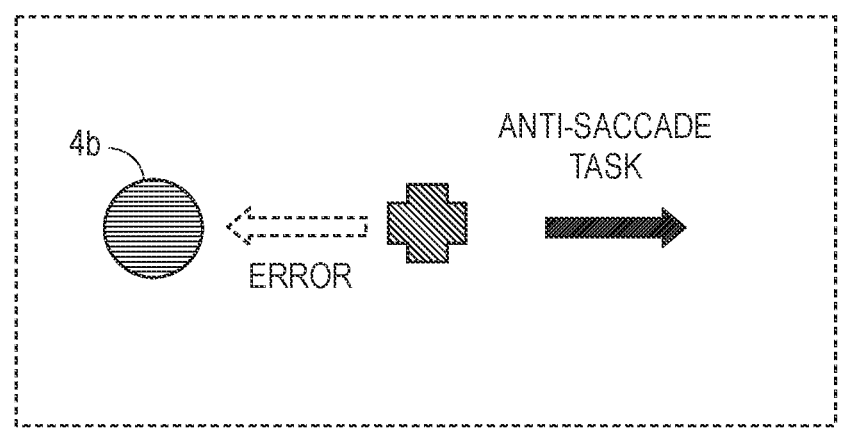
FIG. 2C is a diagram illustrating an inhibitory reflex text administered to a user by the mental impairment detection system, particularly showing an anti-saccade task performed by the user.

The inhibitory reflex test can take many forms; however, in the preferred embodiment of the non-invasive impairment detection system, the inhibitory reflex test comprises at least one anti-saccade task to evoke anti-saccadic eye movements of the user, and at least one pro-saccade task to evoke saccadic eye movements of the user. A saccade is a rapid, simultaneous, movement of both eyes that abruptly change the point of fixation of an individual. The inhibitory reflex test in this case is administered by displaying a motionless target 2 in the field of view of the user, as illustrated in FIG. 2A, instructing the user to fixate on the motionless target 2, randomly presenting different visual stimuli 4*a*, 4*b* (e.g., having different colors) one-at-a-time in the periphery of the field of view of the user, and instructing the user, before any stimuli are presented, to move his or her eyes towards the peripheral visual stimulus 4*a* only when presented to the user (pro-saccade task), as illustrated in FIG. 2B, and opposite or 180 degrees away from the peripheral visual stimulus 4*b* (anti-saccade task) only when presented to the user, as illustrated in FIG. 2C.

The pro-saccade task is naturally reflexive (i.e., the bottom-up reflexive process is engaged) and will produce fast eye movements (short reaction times) with little to no errors (incorrect eye movements away from the visual stimulus) from the user, whereas the anti-saccade task requires the user to inhibit or suppress his or her reflexive desire to look towards the visual stimulus (i.e., the top-bottom inhibitory process is engaged), resulting in slower eye movements (longer reaction times) and more errors (incorrect eye movements towards the visual stimulus).

Figures 3A, 3B:
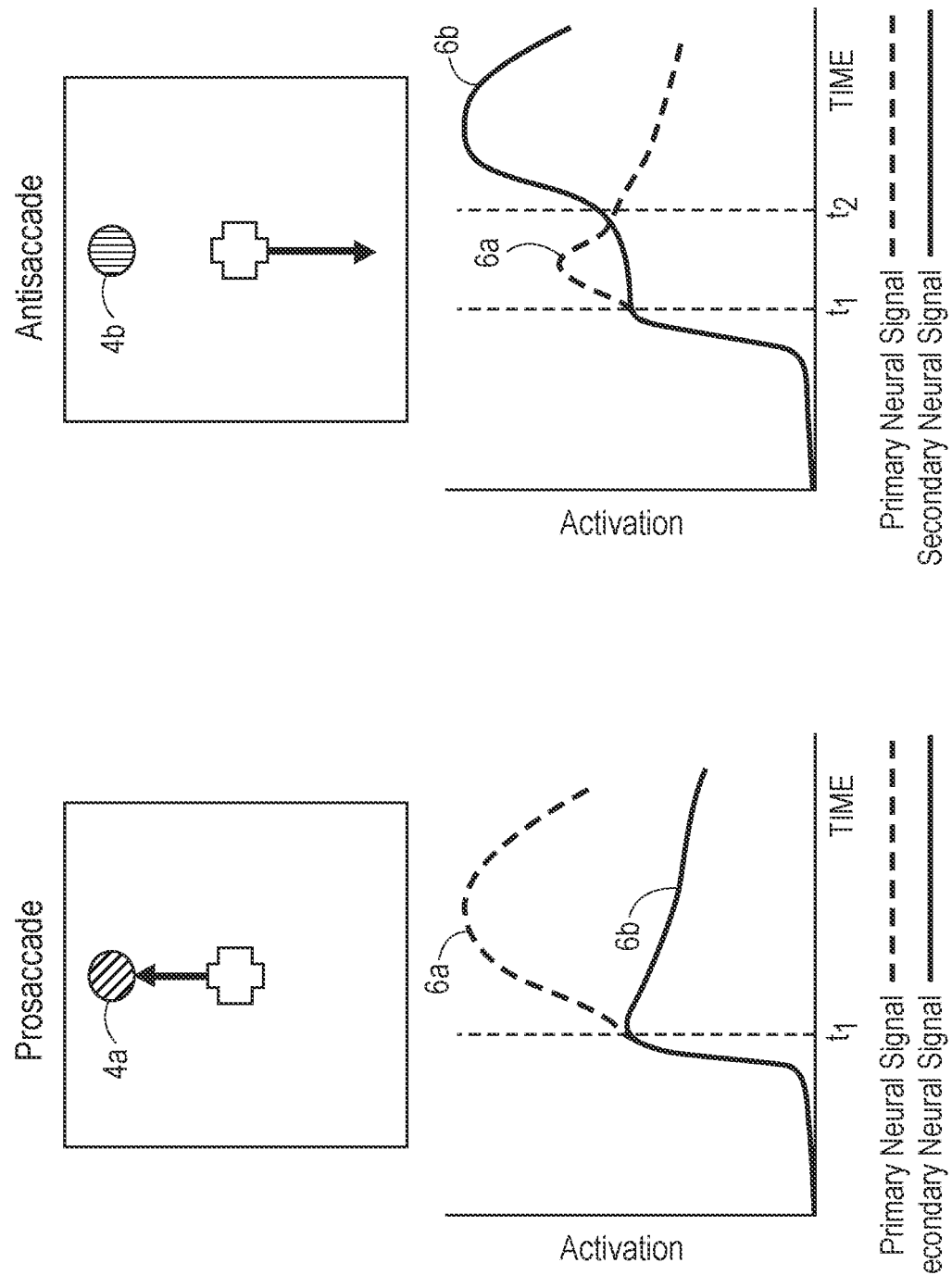
FIGS. 3A and 3B are diagrams illustrating a pro-saccade task and an anti-saccade task and plans generated by the pro-motor cortex of the user to perform the pro-saccade task and anti-saccade task.

The brain signals that are sensed in the premotor cortex of the user during the administration of the inhibitory reflex test reveal sub-threshold premotor signals that are building to elicit eye movements. For example, as illustrated in FIG. 3A, during the pro-saccade task (when the user is instructed to look towards the visual stimulus), a clear and strong primary neural signal 6*a* in the premotor cortex that represents a plan of action to look towards the peripheral stimulus 4*a*, builds and surpasses, at time $t_1$, a much weaker secondary neural signal 6*b* in the premotor cortex that represents a plan of action to look away from the peripheral stimulus 4*a*, eventually triggering eye movements towards the peripheral stimulus 4*a*. In contrast, as illustrated in FIG. 3B, during the anti-saccade task (when the user is instructed to look away from the visual stimulus), the top-down inhibitory process is engaged to plan an action to look away from the peripheral stimulus 4*b*, thereby suppressing the normally stronger primary neural signal 6*a* representing the plan of action to look towards the peripheral stimulus 4*b*, at time $t_1$, and facilitating the normally weaker secondary neural signal 6*b* representing the plan of action to look away from the peripheral stimulus 4*b* to surpass the primary neural signal 6*a*, at time $t_2$, eventually triggering eye movements away from the peripheral stimulus 4*b*.

The manifestation of the neural signals 6*a*, 6*b* (shown in FIG. 3B) occurs prior to eye movements, and thus, provides insight into the eye movements prior to actual movement of the eyes. When an individual is mentally impaired, his or her ability to suppress the primary neural signal 6*a* during the anti-saccade task is significantly compromised. Thus, the secondary neural signal 6*b* (i.e., the signal resulting from the top-down inhibitory process that suppresses the normally strong primary signal 6*b*) reveals attenuated neural dynamics that struggle to engage top-down inhibitory process, and therefore, elicit erroneous behavior. In contrast, the primary neural signal 6*a* (shown in FIG. 3A) measured during the pro-saccade task will not be significantly compromised when an individual is mentally impaired.

Figure 4B:
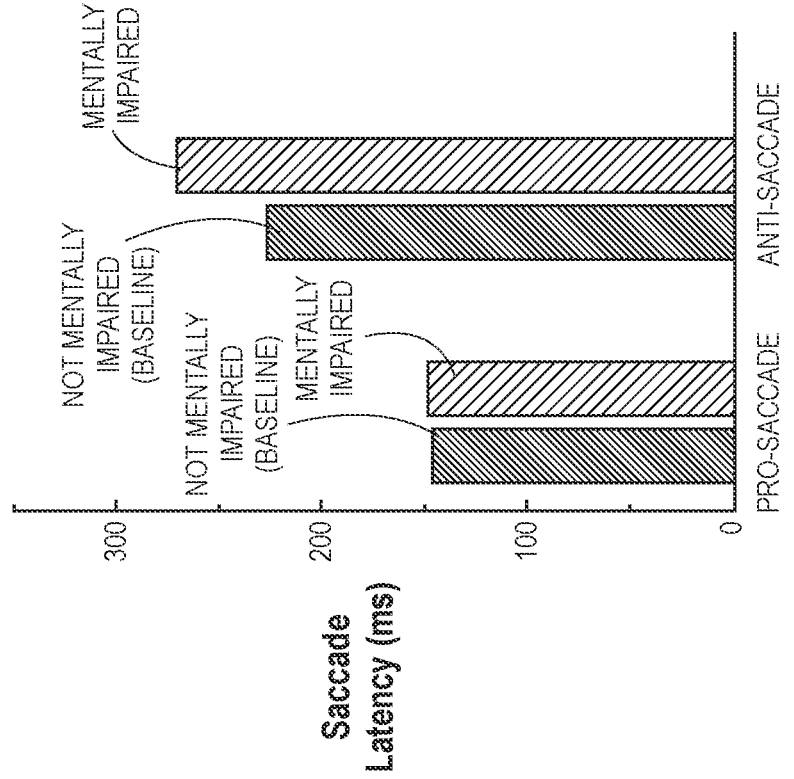
FIG. 4B is a bar diagram illustrating an exemplary saccade latency of the performance of pro-saccade tasks in an inhibitory reflex test administered by the mental impairment detection system to the user when the user is not mentally impaired and when the user is mentally impaired, and an exemplary saccade latency of the performance of anti-saccade tasks in an inhibitory reflex test administered by the mental impairment detection system to the user when the user is not mentally impaired and when the user is mentally impaired.
Figure 4A:
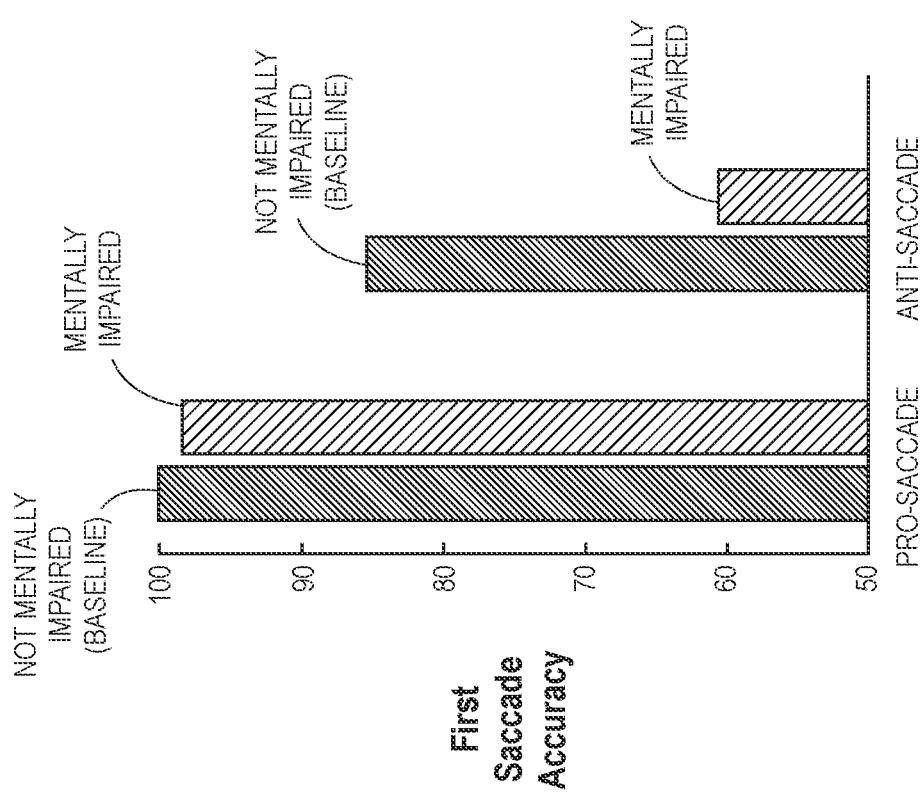
FIG. 4A is a bar diagram illustrating an exemplary first saccade accuracy of the performance of pro-saccade tasks in an inhibitory reflex test administered by the mental impairment detection system to the user when the user is not mentally impaired and when the user is mentally impaired, and an exemplary first saccade accuracy of the performance of anti-saccade tasks in an inhibitory reflex test administered by the mental impairment detection system to the user when the user is not mentally impaired and when the user is mentally impaired.

Thus, it can be appreciated from the foregoing that the difference between pre-motor responses of an individual when not mentally impaired and when mentally impaired will be very similar during the performance of a pro-saccade task, but will significantly be different during the performance of an anti-saccade task. Over a period of time when an inhibitory reflex test comprising many pro-saccade tasks and anti-saccade tasks is performed on an individual, bi-modal measurements (pro-saccade and anti-saccade) of the individual can be quantified. For example, the bi-modal measurements for an individual can be quantified in terms of both accuracy (errors) for an individual when not mentally impaired (baseline) and for the same individual when mentally impaired (FIG. 4A), and reaction time for an individual when not mentally impaired (baseline) and for the same individual when mentally impaired (FIG. 4B). As shown in FIG. 4A, the first saccade accuracy (shown as percentage accuracy) for the individual when performing pro-saccade tasks is virtually 100 percent for both the non-mentally impaired case and the mentally impaired case. In stark contrast, as also shown in FIG. 4A, the first saccade accuracy for the individual when performing anti-saccade tasks is about 85 percent in the non-mentally impaired case, and 60 percent in the mentally impaired case. As shown in FIG. 4B, the saccade latency for the individual when performing pro-saccade tasks is 150 ms for both the non-mentally impaired case and the mentally impaired case. In stark contrast, as also shown in FIG. 4B, the saccade latency for the individual when performing anti-saccade tasks is about 225 ms in the non-mentally impaired case, and 275 ms in the mentally impaired case.

Thus, it can be appreciated that measurements (either or both first saccade error and saccade latency) taken when an individual is performing anti-saccade tasks can be compared to baseline measurements (when the individual is not mentally impaired) to ascertain the current level of mental impairment of the individual.

Figure 5:
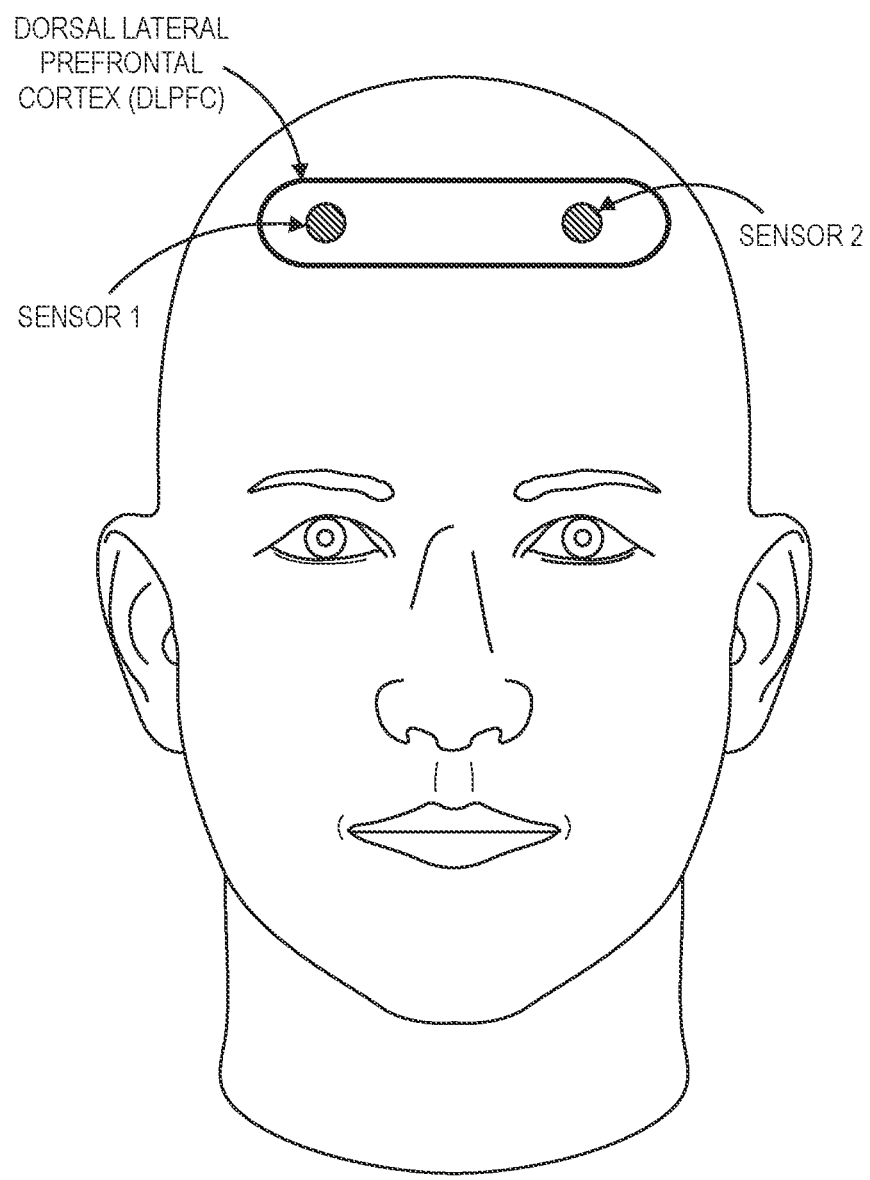
FIG. 5 is a front view of a head of a person, particularly illustrating sensors used by non-invasive mental impairment detection system constructed in accordance with one embodiment of the present inventions to detect brain activity from the dorsal lateral prefrontal cortex (DLPFC) of a user.

Although the inhibitory reflex test has been described in terms of pro-saccade tasks and anti-saccade tasks, an inhibitory reflex test may comprise other types of tasks, such as go/no-go tasks, which measures the capacity of an individual for sustained attention and response control. In this case, the brain activity of the dorsal lateral prefrontal cortex (DLPFC) in the frontal lobe of the user is bilaterally measured, as illustrated in FIG. 5. The DLPFC is an area in the prefrontal cortex of the brain (in the forehead), and is believed to play a role in sustained attention. The DLPFC responds to increased working memory demand on both go and no-go tasks, and is thought to be involved in accessing sustained task information, alerting, or autonomic changes when cognitive demands increase. Without this function, the user would lack response inhibition.

Each stimulus of this type of inhibitory reflex test either indicates a "Go" task or a "No-Go" task. The inhibitory reflex test in this case is performed by randomly or pseudo-randomly presenting (e.g., auditory, visual, or tactile) different stimuli (e.g., different colors or sounds or vibrations) one-at-a-time to the user, and instructing the user, before any stimuli are presented, to perform an action (e.g., moving a forefinger) if a "Go" stimulus is presented to the user, and to not perform the action (e.g., by not moving a forefinger) if a "No-Go" stimulus is presented to the user.

When an individual is mentally impaired, his or her ability to focus is significantly compromised. Thus, a neural signal resulting from a top-down inhibitory process that suppresses a plan to perform the designated action (moving a forefinger) reveals attenuated neural dynamics that struggle to engage top-down inhibitory process that result in errors (i.e., performing the designated action when presented with a "No-Go" stimulus. Furthermore, the working memory of the individual, which can be assessed from the DLPFC and frontal eye fields (pre-motor cortex) is also compromised, and will cause errors on the no-go tasks, as well as compromised inhibitory reflex. The difference between pre-motor responses of an individual when not mentally impaired and when mentally impaired will be significantly different during the performance of the no-go task. Thus, it can be appreciated that measurements taken when an individual is performing go/no-go tasks can be compared to baseline measurements (when the individual is not mentally impaired) to ascertain the current level of mental impairment of the individual.

In another embodiment, rather than instructing the user to perform inhibitory reflex tasks, the user may be instructed to perform sustained-attention tasks that do not require inhibitory reflex functions. For example, the user may be instructed to perform a psychomotor vigilance task (PVT), which is a sustained-attention, reaction-timed task that measures the speed with which an individual may respond to a visual stimulus. In this case, the brain activity of the DLPFC of the user is bilaterally measured, as previously illustrated in FIG. 5. The sustained-attention test in this case is performed by randomly or pseudo-randomly presenting a visual stimulus every few seconds over a period of time (e.g., 5-10 minutes), and instructing the user, before any stimuli are presented, to perform an action (e.g., moving a forefinger) in response to each stimulus. Research indicates that mental impairment of an individual (such as lack of sleep or sleep deficit) correlates with deteriorated alertness, slower problem-solving, declined psycho-motor skills, and increased rate of false responding. The purpose of the PVT is to measure sustained attention. The result of this sustained attention test can be quantified as a numerical measure of the number of false responses (i.e., the number of times the designated action is performed in response to no stimulus).

The mental impairment detection system described herein can perform supplemental measurements of the user in additional to the inhibitory reflex test (or alternatively, sustained attention test) described above. For example, the mental impairment detection system can additionally track head movements of the user to provide insight towards abnormal vestibular movements that can be correlated to mental impairments, such as drug and/or alcohol impairments, and determine the level of mental impairment of the user further based on these tracked head movements. As in the cases described above, the tracked head movements may be compared to a baseline measurement of head movements acquired when it is known that that the user is not mentally impaired, to determine whether or not the user is currently mentally impaired.

As another example, the mental impairment detection system can additionally administer a reflex test in the form of a sensory stimulus (e.g., visual, auditory, or tactile) to the user, and detect brain activity in one of the reflex circuits in the brain of the user in response to a sensory stimulus, and determine the level of mental impairment of the user further based on the detected reflex activity. Such reflex circuits may include, e.g., reflex loops between the parietal lobe and motor cortex, somatosensory cortex, auditory cortex, and frontal regions of the brain that influence eye movements, hand movements, touch, coordination, etc., or frontal loops carrying auditory signals or visual signals to the DLPFC. As in the cases described above, the detected reflex circuits may be compared to a baseline measurement of the reflex circuits acquired when it is known that that the user is not mentally impaired, to determine whether or not the user is currently mentally impaired.

Figure 6:
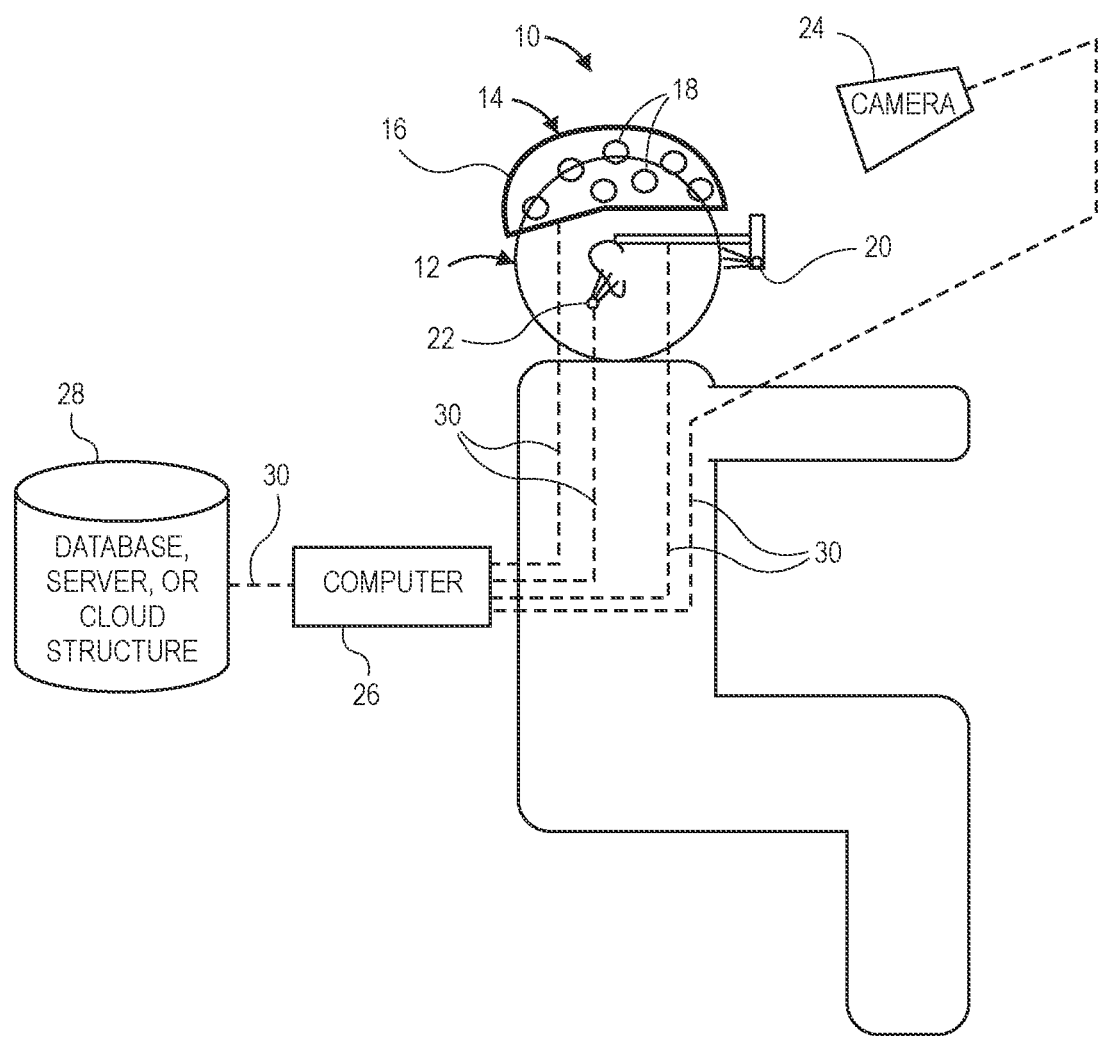
FIG. 6 is a pictorial diagram of the non-invasive mental impairment detection system.

Referring now to FIG. 6, a generalized embodiment of a non-invasive mental impairment system 10 constructed in accordance with the present inventions will be described. The non-invasive mental impairment system 10 is configured for administering an inhibitory reflex test (or alternatively a sustained attention test) to a user 12, e.g., one or more of the inhibitory reflex tests (or sustained attention tests) described above, detecting brain activity in the frontal lobe of the user 12 (e.g., in the pre-frontal cortex or DLPFC) while the user 12 performs the inhibitory reflex test (or sustained attention tests), and determining a level of mental impairment of the user 12 based on the brain activity detected in the frontal lobe of the user 12.

To this end, the non-invasive mental impairment system 10 comprises a non-invasive brain interface assembly 14 configured for detecting brain activity of a user 12. The non-invasive brain interface assembly 14 comprises a plurality of sensors 18 configured for being placed on or near the head of the user 12 with access to the top front (premotor cortex) and/or forehead (DLPFC) of the user 12, as respectively illustrated in FIGS. 1 and 5. The sensors 18 may detect the neural data signals at a reasonably fast sample rate, e.g., 100 Hz or more.

In the preferred embodiment, the brain interface assembly 14 has a form-factor that is portable and easily worn on the head of user 12 for use in a normal life or work environment, while using high fidelity processes to acquire high quality neural signals with high spatial resolution from the user. In this case, the brain interface assembly 14 comprises a support structure 16 configured for being worn on the head of the user 12. The sensors 18 are arranged on the support structure 16, such that the sensors 18 are disposed around the head of the user 12. The support structure 16 may be shaped, e.g., have a headband, cap, helmet, beanie, other hat shape, or other shape adjustable and conformable to the head of the user 12. Further details discussing different form factors of brain interface assemblies are set forth in U.S. Provisional Patent Application Ser. No. 62/829,124, entitled "Modulation of Mental State of a User Using a Non-Invasive Brain Interface System and Method," and U.S. Non-Provisional Ser. No. 16/364,338, entitled "Biofeedback for Awareness and Modulation of Mental State Using a Non-Invasive Brain Interface System and Method," which are both expressly incorporated herein by reference.

The non-invasive brain interface assembly 14 can be programmed to specifically target brain activity in the pre-motor cortex or DLPFC of the frontal region of the brain of the user 12, e.g., activating certain ones of the sensors 18 covering the pre-motor cortex or DLPFC. Alternatively, the brain interface assembly 14 may be specifically designed, such that only sensors 18 that cover the pre-motor cortex or DLPFC are disposed on the support structure 16 in the regions corresponding to the pre-motor cortex or DLPFC. The brain interface assembly 14 can also be programed or specifically designed to target brain activity in other regions of the brain, e.g., when detecting reflex activity in response to the presentation of a reflex test to the user 12.

In an alternative embodiment, an extendable arm (not shown) carrying the sensors 18 may release from the head rest of a vehicle and sit comfortably on the head of the user 12 (in this case, the driver). In another alternative embodiment, the sensors 18 may be embedded in the ceiling and side walls of the vehicle that have a field of view to the head of the user (driver) 12.

In any event, the brain interface assembly 14 is preferably an optically-based non-invasive brain interface assembly, in which case, the sensors 18 may comprise, e.g., a single photon avalanche diode (SPAD) array, avalanche photodiode array, metal semiconductor photodiode array, etc., and may be associated with pulsed, chirped, or continuous wave light sources, or a magnetically-based non-invasive brain interface assembly, in which case, the sensors 18 may comprise, e.g., an atomic vapor cell, nitrogen vacancy diamond, or giant magnetoresistance.

Optically-based non-invasive brain interface assemblies may, e.g., incorporate any one or more of the neural activity detection technologies described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration," U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. Provisional Patent Application Ser. No. 62/722,152, entitled "Time-Of-Flight Optical Measurement And Decoding Of Fast-Optical Signals," U.S. Provisional Patent Application Ser. No. 62/781,098, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Patent Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Patent Application Ser. No. 62/855,360, entitled "Interferometric Parallel Detection Using Digital Rectification and Integration", U.S. Provisional Patent Application Ser. No. 62/855,380, entitled "Interferometric Parallel Detection Using Analog Data Compression," and U.S. Provisional Patent Application Ser. No. 62/855,405, entitled "Partially Balanced Interferometric Parallel Detection," which are all expressly incorporated herein by reference.

If the optically-based non-invasive brain interface assembly comprises a SPAD system, it may, e.g., incorporate any one or more of the neural activity detection technologies described in U.S. Non-Provisional patent application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340,408), U.S. patent application Ser. No. 16/283,730, entitled "Stacked Photodetector Assemblies," and U.S. Provisional Patent Application Ser. No. 62/844,107, entitled "Power-Efficient Architecture for Time-Correlated Single Photon Counting," which are all expressly incorporated herein by reference.

Magnetically-based non-invasive brain interface assemblies may, e.g., incorporate any one or more of the neural activity detection technologies described in U.S. Provisional Patent Application Ser. No. 62/689,696, entitled "Magnetic Field Measurement Systems and Methods of Making and Using," U.S. Provisional Patent Application Ser. No. 62/732,327, entitled "Variable Dynamic Range Optical Magnetometer and Methods of Making and Using", U.S. Provisional Patent Application Ser. No. 62/741,777, entitled, "Integrated Gas Cell and Optical Components for Atomic Magnetometry and Methods for Making and Using," U.S. Provisional Patent Application Ser. No. 62/752,067, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," U.S. Provisional Patent Application Ser. No. 62/732,791, entitled "Dynamic Magnetic Shielding and Beamforming Using Ferrofluid for Compact Magnetoencephalography (MEG)," U.S. Provisional Patent Application Ser. No. 62/796,958, entitled "Optically Pumped Magnetometer with Amplitude-Selective Magnetic Shield," and U.S. Provisional Patent Application Ser. No. 62/804,539, entitled "Neural Bandpass Filters for Enhanced Dynamic Range Magnetoencephalography (MEG) Systems and Methods," which are all expressly incorporated herein by reference.

Optically-based or magnetically-based non-invasive brain interface assemblies should be contrasted with electroencephalography (EEG) or functional magnetic resonance imaging (fMRI) brain interface assemblies that are limited in their form factor and have limitations on spatial resolution, and thus, currently cannot effectively acquire neural signals from the user 12 in a normal life or work environment.

In particular, fMRI requires large magnets enclosed within a tunnel tube-type enclosure that patients lie within (similar to magnetic resonance imaging (MRI) machines) which are known to cause claustrophobia, and thus, cannot be scaled to wearable or portable form factors. EEG does not provide spatial information and is susceptible to noise and artifacts from the skull and other brain tissue (e.g., if the user wiggles his or her eyebrows, blinks, or performs any number of other movements in a vehicle). Furthermore, an EEG-based brain interface assembly is difficult to interface or coupled with the brain. For example, in order to obtain a signal, EEG electrodes require the use of a "conductive gel," since the electrodes need to be "wet" in order to bridge the gap between skin and the EEG electrodes. Also, in order to have an effective EEG recording, the EEG electrodes are required to be in direct contact with the user's skull. Also, users typically experience pressure and discomfort when wearing an EEG-based brain interface assembly, and removal of the gel from user's hair often requires a special washing solution since the gel is known to have an adhesive effect on the hair and skull.

The non-invasive mental impairment system 10 further comprises a sensory stimulation device 20 configured for administering the inhibitory reflex test to the user 12. In the preferred embodiment, the sensory stimulation device 20 comprises a display device configured for displaying the inhibitory reflex test to the user 12. In the illustrated embodiment, the display device 20 comprises a head mounted display (HMD), such as, e.g., virtual reality (VR) glasses. Alternatively, the display device 20 may comprise a heads-up display unit, a windshield on a car on which the inhibitory reflex test is displayed by a projector built into the dashboard of the car, an infotainment center of the vehicle, etc.

The non-invasive mental impairment system 10 further comprises a communications device 22 configured for communicating instructions for the inhibitory reflex test to the user 12. In the preferred embodiment, the communications device 22 comprises one or more speakers, e.g., headphones or earbuds, that auditorily communicates the instructions for the inhibitory reflex test to the user 12. The non-invasive mental impairment system 10 further comprises an optional camera 24 configured for tracking head movements of the user 12. The camera 24 can be discreetly placed anywhere in a vehicle, so as to not obstruct the field of view of the user (driver) 12.

The non-invasive mental impairment system 10 further comprises a computer 26 (e.g., a Smartphone, tablet computer, or the like) configured for administering the inhibitory reflex test by sending signals to the sensory stimulation device 20 to administer the inhibitory reflex test to the user 12 and to the communications device 22 to communicate the instructions for taking the inhibitory reflex test to the user 12, as well as storing and analyzing the information acquired by the brain interface assembly 14 to ultimately determine a level of mental impairment of the user 12. The computer 26 determines the level of the mental impairment of the user 12 by quantifying the results of the inhibitory reflex test taken by the user 12, effectively grading the inhibitory reflex test, and comparing these quantified results to the baseline results of the inhibitory reflex test taken by the user 12 when known to be not mentally impaired. The manner in which the computer 26 quantifies the results of the inhibitory reflex test will ultimately depend on the nature of the inhibitory reflex test.

For example, if the inhibitory reflex test comprises pro-saccade/anti-saccade tasks, the computer 26 may quantify the results of the inhibitory reflex test by determining the first saccade accuracy (see FIG. 4A) and/or saccade latency (see FIG. 4B) for the anti-saccade tasks performed by the user 12 over the duration of the inhibitory reflex test. If the inhibitory reflex test comprises go/no-go tasks, the computer 22 may quantify the results of the inhibitory reflex test by determining the number of errors (the number of times user 12 erroneously performs the designated action in the presence of a "No-Go" stimulus) for the No-Go tasks over the duration of the inhibitory reflex test. If the inhibitory reflex test comprises a PVT, the computer 26 may quantify the results of the inhibitory reflex test by determining the number of lapses in attention of the user 12 (the number of times the designated action is not performed in response to a stimulus).

Any one of a variety of data models can be used to classify the results of the inhibitory reflex test taken by the user 12, and will highly depend on the characteristics of brain activity that are input onto the data models. Such characteristics of brain activity may typically be extracted from the spatiotemporal brain activity that is captured, and can include, e.g., location of signal, fine grained pattern within or across locations, amplitude of signal, timing of response to behavior, magnitude of frequency bands of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of the brain activity can be extracted from preprocessed raw data recorded during the inhibitory reflex test. The preprocessing of the raw data typically involves filtering the data (either in the time domain or the frequency domain) to smooth, remove noise, and separate different components of signal. Data models can include, e.g., support vector machines, expectation maximization techniques, naïve-Bayesian techniques, neural networks, simple statistics (e.g., correlations), deep learning models, pattern classifiers, etc.

The data model is typically initialized with some training data (meaning that a calibration routine can be performed on the user 12). If no training information can be acquired, such data model can be heuristically initialized based on prior knowledge, and the data models can be iteratively optimized with the expectation that optimization will settle to some optimal maximum or minimum solution. A data model that has already been proven, for example, in a laboratory setting, can be initially uploaded to the non-invasive mental impairment detection system 10, which system will then use the uploaded data models to quantify the results of the inhibitory reflex test taken by the user 12. Optionally, the non-invasive mental impairment detection system 10 may collect data during actual use with the user 12, which can then be downloaded and analyzed in a separate server, for example in a laboratory setting, to create new or updated data models. Software upgrades, which may include the new or updated data models, can be uploaded to the non-invasive mental impairment detection system 10 to provide new or updated data modelling and data collection.

The non-invasive mental impairment detection system 10 optionally comprises a database, server, or cloud structure 28 configured for tracking the brain activity of the user 12. For example, the database, server, or cloud structure 28 may be configured to collect raw data (e.g., brain activity data) generated by the brain interface assembly 14. Furthermore, the database, server, or cloud structure 28 (independently of or in conjunction with the mental impairment functions of the computer 26) may be configured for performing a data analysis of the raw data in order to determine the level of mental impairment of the user 12.

For example, if the raw data obtained by the user 12 is being anonymized and stored in the database, server, or cloud structure 28, the data models can be pooled across various users, which deep learning algorithms would benefit from. The database, server, or cloud structure 28 may be configured for performing cross-correlation analysis of the signal data analysis in order to reduce the pool size of the database and focus subject averaged data to a pool that is similar to the user 12. Most likely, each user 12 will have a portion of their data model optimized to them, but then another portion takes advantage of patterns extracted from a larger pool of users. Generalizing data models may comprise various variabilities and optimizing may be difficult. However, by building a large user database on the database, server, or cloud structure 28, a data analysis pipeline connected to such database, server, or cloud structure 28 can preprocess data (clean it up), extract all different kinds of features, and then apply an appropriate data model, to overcome this issue. Although, all of the tracked data analysis has been described as being performed by the database, server, or cloud structure 28, it should be appreciated that at least a portion of the tracked data analysis functionality may be incorporated in the computer 26, with the caveat that it is preferred that the tracking of the brain activity between a pool of users be performed by the database, server, or cloud structure 28.

The computer 26 may be coupled to the non-invasive brain assembly 14, display device 20, communications device 22, camera 24, and database, server, or cloud structure 28 via wired or wireless communications links (e.g., wireless radio frequency (RF) signals (e.g., Bluetooth, Wifi, cellular, etc.) or optical links (e.g., fiber optic or infrared (IR)) 30.

Figure 7A:
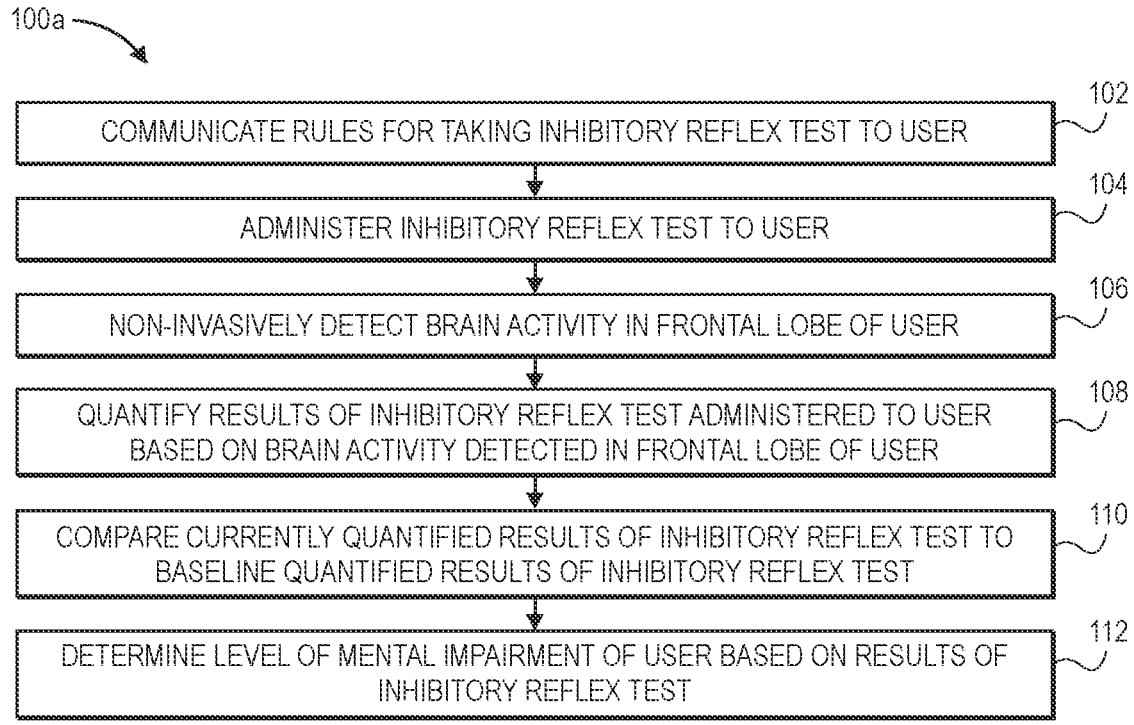
FIG. 7A is a flow diagram illustrating one method performed by the non-invasive mental impairment detection system to detect mental impairment in the user using an inhibitory reflex test.

Having described the structure, function, and application of the non-invasive mental impairment detection system 10, one method 100a of operating the mental impairment detection system 10 will now be described with reference to FIG. 7A. It should be appreciated that, although the method 100a is described in the context of an inhibitory reflex test, a method can utilize a sustained reflex test as an alternative, or in addition, to the inhibitory reflex test.

First, the mental impairment detection system 10 communicates (e.g., via the communications device 22) the rules for taking the inhibitory reflex test to the user 12 (step 102). For example, if the inhibitory reflex test comprises pro-saccade and anti-saccade tasks, the mental impairment detection system 10 instructs the user 12 to fixate on the motionless target 2, make a saccade in a direction towards the first visual stimulus 4a (if it has a certain characteristic, e.g., purple) and make a saccade in a direction away from the second different visual stimulus 4b (if it has a certain characteristic, e.g., red) (see FIGS. 2A-2C).

Then, the mental impairment detection system 10 administers the inhibitory reflex test by displaying the inhibitory reflex test via the sensory stimulation device 20) to the user 12 (step 104). For example, if the inhibitory reflex test comprises pro-saccade and anti-saccade tasks, the mental impairment detection system 10 randomly or pseudo-randomly displays the first and second visual 4a, 4b stimuli one at a time in the periphery of the field of the vision of the user 12.

The mental impairment detection system 10 (via the non-invasive brain interface assembly 14) then non-invasively detects brain activity in the frontal lobe of the user 12 while the inhibitory reflex test is administered to the user 12 (step 106). For example, if the inhibitory reflex test comprises pro-saccade and anti-saccade tasks, brain activity in the premotor cortex of the user 12 may be non-invasively detected.

The mental impairment detection system 10 (via the computer 26) then quantifies results of the inhibitory reflex test administered to the user 12 based on the brain activity detected in the frontal lobe of the user 12 (step 108). For example, if the inhibitory reflex test comprises pro-saccade and anti-saccade tasks, the mental impairment detection system 10 may compute a percentage of errors and/or an average latency time for all anti-saccade tasks performed during the administration of the inhibitory reflex.

Then, the mental impairment detection system 10 (via the computer 26) compares the currently quantified results of the inhibitory reflex test (i.e., the quantified results of the inhibitory reflex test currently administered to the user 12) to baseline quantified results of the inhibitory reflex test (i.e., the quantified results of the inhibitory reflex administered to the user 12 when the user 12 is known to not be mentally impaired) (step 110). Such comparison function may comprise computing the difference between the currently quantified results of the inhibitory reflex test to the baseline quantified results of the inhibitory reflex test.

The baseline quantified results can be previously acquired by administering the same inhibitory reflex test to the user 12 when the user 12 is known to not be mentally impaired, i.e., communicating the rules for taking the inhibitory reflex test to the user 12, administering the inhibitory reflex test to the user 12, non-invasively detecting brain activity in the frontal lobe of the user 12 while the inhibitory reflex test is administered to the user 12, and quantifying the results of the inhibitory reflex test administered to the user 12 based on the brain activity detected in the frontal lobe of the user 12.

The mental impairment detection system 10 (via the computer 26) then determines the level of mental impairment (if any) of the user 12 based on the comparison between the currently quantified results of the inhibitory reflex test and the baseline quantified results of the inhibitory reflex test (step 112). For example, the mental impairment detection system 10 may access a look-up table comprising different reference levels of mental impairment for the user 12 correlated to a range of reference differences (i.e., differences between the quantified results of the inhibitory reflex test and the baseline quantified results of the inhibitory reflex test), and selecting the reference level of mental impairment correlated to the reference difference that matches the computed difference between the currently quantified results of the inhibitory reflex test and the baseline quantified results of the inhibitory reflex test.

The mental impairment detection system 10 may optionally confirm or supplement the quantified results of the inhibitory reflex test used to determine the level of mental impairment of the user 12 at step 112.

Figure 7B:
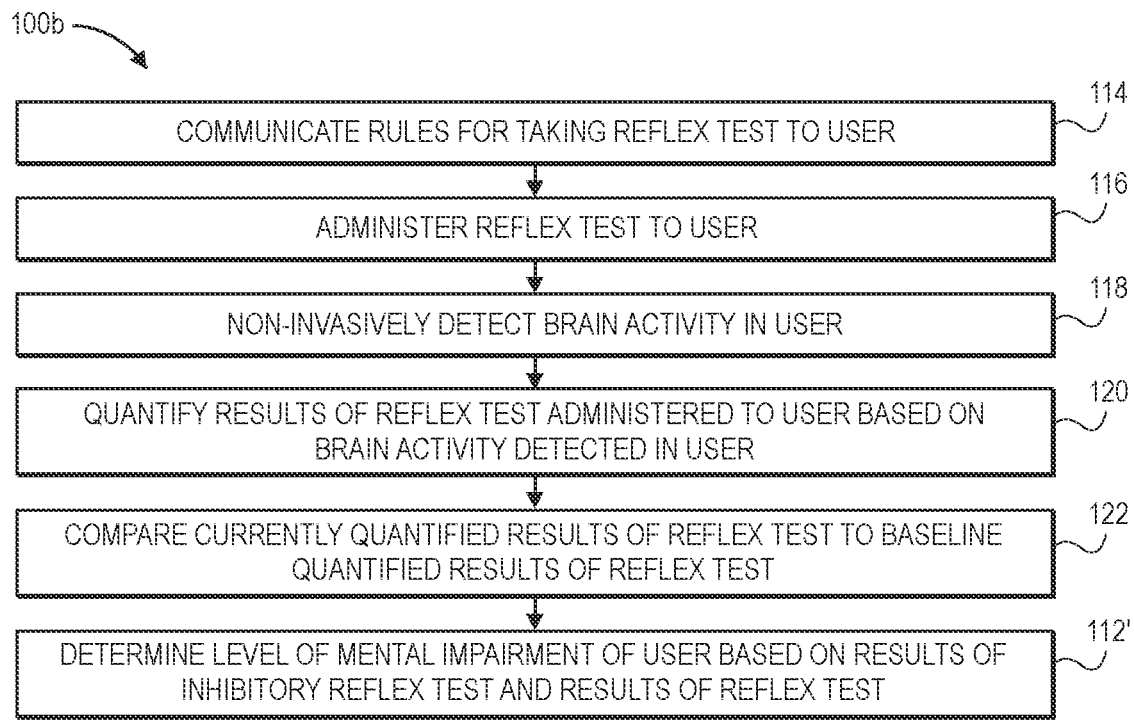
FIG. 7B is a flow diagram illustrating one method performed by the non-invasive mental impairment detection system to detect mental impairment in the user using a reflex test in addition to the inhibitory reflex test performed in the method of FIG. 7A.

For example, one method 100b of operating the mental impairment detection system 10 to supplement the quantified results of the inhibitory reflex test with quantified results of a reflex test will now be described with reference to FIG. 7B.

In this case, the mental impairment detection system 10 (e.g., via the communications device 22) may communicate the rules for taking a reflex test to the user 12 (step 114); administers the reflex test (e.g., by displaying the reflex test via the sensory stimulation device 20) to the user 12 (step 116); non-invasively detects brain activity in the brain of the user 12 (via the non-invasive brain interface assembly 14) while the reflex test is administered to the user 12 (step 118), quantifies the results of the reflex test administered to the user 12 based on the brain activity detected in the brain of the user 12 (step 120), and compares the quantified results of the reflex test administered to the user 12 to baseline quantified results of the reflex test administered to the user 12 when the user 12 is known to not be mentally impaired (step 122). The mental impairment detection system 10 (via the computer 26) then determines the level of mental impairment of the user 12, based on the comparison between the currently quantified results of the inhibitory reflex test and the baseline quantified results of the inhibitory reflex test, in conjunction with or confirmed by a comparison between the currently quantified results of the reflex test and the baseline quantified results of the reflex test (step 112').

Figure 7C:
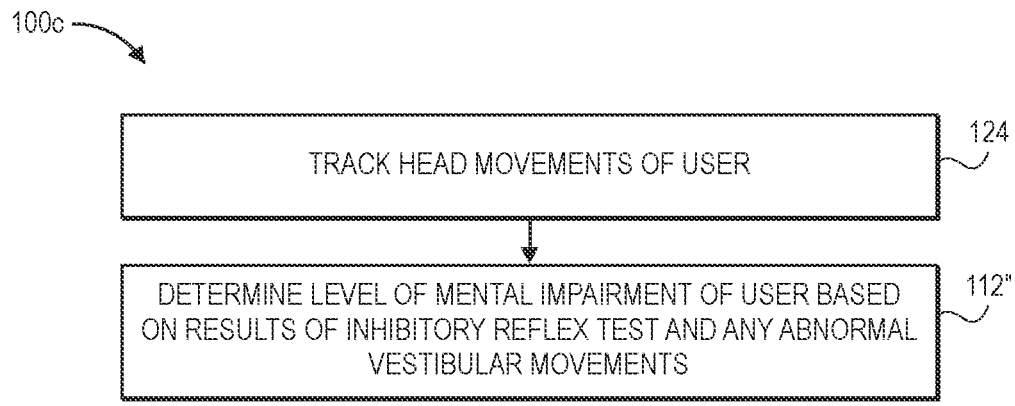
FIG. 7C is a flow diagram illustrating one method performed by the non-invasive mental impairment detection system to detect mental impairment in the user by tracking head movements of the user in addition to the inhibitory reflex test performed in the method of FIG. 7A.

As another example, another method 100c of operating the mental impairment detection system 10 to supplement the quantified results of the inhibitory reflex test with quantified results of head tracking will now be described with reference to FIG. 7C. The mental impairment detection system 10 (via the camera 24) may track the head movements of the user (step 124). The mental impairment detection system 10 may then determine the level of mental impairment of the user 12 based on the comparison between the currently quantified results of the inhibitory reflex test and the baseline quantified results of the inhibitory reflex test, in conjunction with or confirmed by any abnormal vestibular movements that can be correlated to mental impairments of the user (step 112").

In an alternative embodiment, a non-invasive spatial attention control system (FIG. 8) may be similar to the non-invasive mental impairment detection system 10 described above, with the exception of, instead of detecting mental impairment of the user 12, the spatial attention control system allows the user 12 to spatially control a virtual menu merely by envisioning the menu in the mind of the user 12 and mind controlling the virtual menu, thereby freeing the hands of the user to perform other tasks, while also allowing the user 12 to focus his or her eyes on objects necessary to safely perform such tasks. Thus, the spatial attention control system particularly lends itself to situations where the user 12 must maintain eye contact on a particular task (e.g., looking at the road during operation of transportation vehicles, such as cars, motorcycles, and trucks; looking at a landing strip when flying an airplane; looking at air traffic as an air traffic controller, or looking at payloads when operating heavy machinery, etc.

Figure 8:
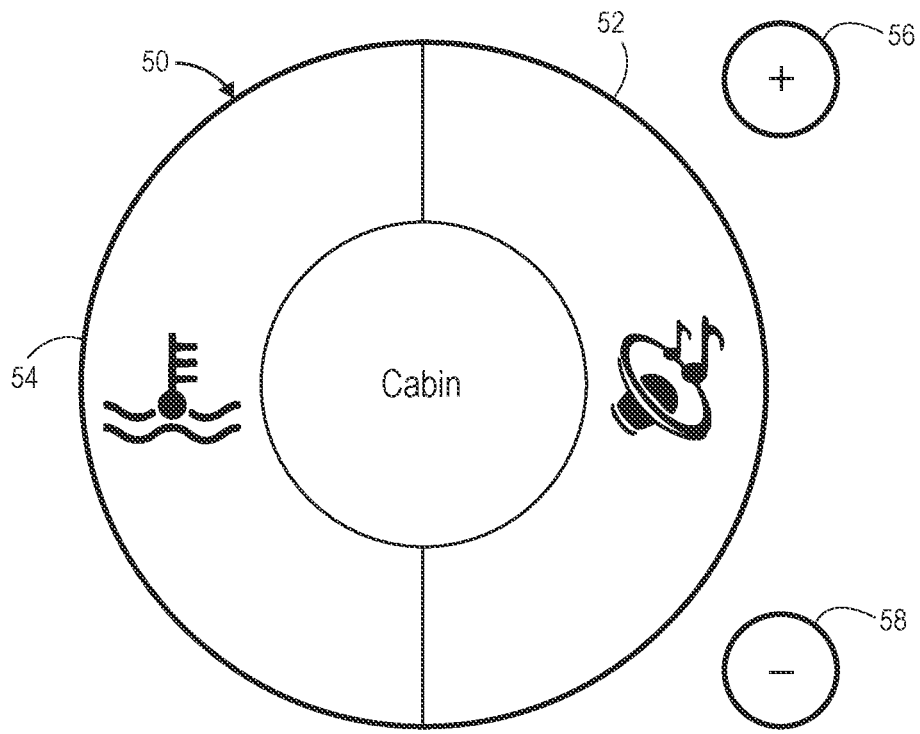
FIG. 8 is a pictorial diagram of a virtual radial menu used by a non-invasive spatial attention control system that allows a user to spatially control the virtual radial menu via mind control.

To this end, the user 12 envisions a specific virtual menu, such as the virtual radial menu 50 illustrated in FIG. 8. The user 12 controls the virtual radial menu 50, while still focusing his or her attention on the task at hand (e.g., maintaining eye contact with the road if the user 12 is driving a car), by covertly shifting his or her spatial attention in any direction depending on what functions on the virtual radial menu 50 the user 12 wants to control. If, for example, the user (driver) 12 can shift his or her covert spatial attention to the right to access music and radio channel options 52 or to the left to access temperature control 54 of the cabin. After selecting the music or radio channel options 52 or the temperature control 54, the user 12 can then covertly shift his or her spatial attention to the up button 56 or the down button 58 to control the volume of the music or the temperature in the cabin.

The virtual radial menu 50 may be memorized by the user 12 beforehand, and therefore does not need to be displayed, or optionally can be displayed by the display device 20 illustrated in FIG. 6. The non-invasive spatial attention control system may utilize the non-invasive brain interface assembly 14 to detect brain activity in the pre-motor cortex and/or DLPFC of the user 12, and the computer 26 and/or database, server, or cloud structure 28 may extract features from the detected brain activity correlated to the direction in which the user 12 covertly shifts his or her spatial attention.

Figure 9:
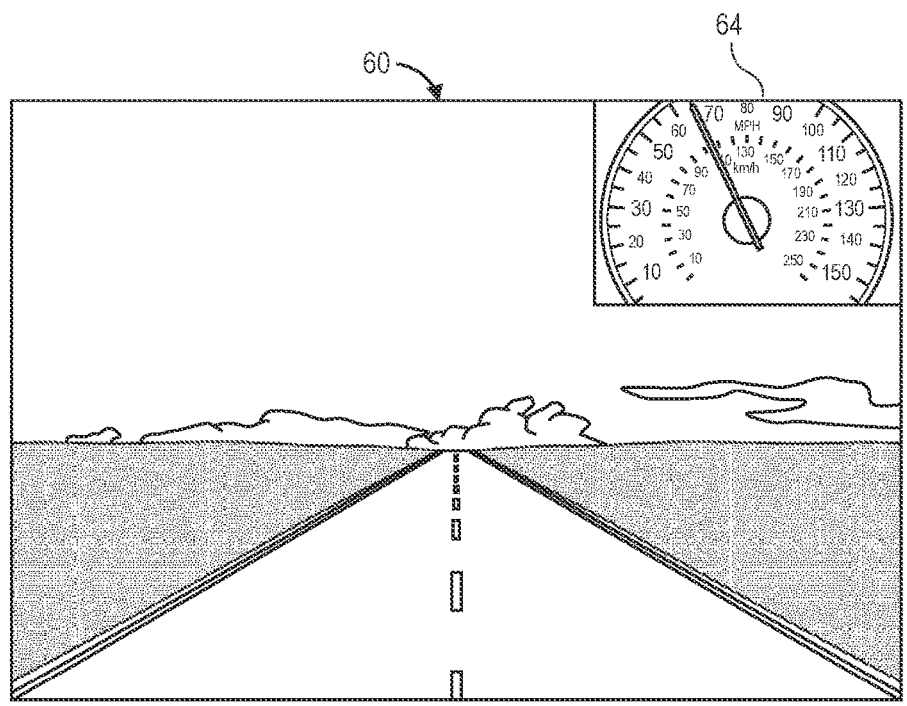
FIG. 9 is a pictorial diagram of a driving scenario generated by a non-invasive driving simulation system that trains a user to optimize concentration on a road.

As another alternative embodiment, a non-invasive driving simulation system may be similar to the non-invasive mental impairment detection system 10 described above, with the exception of, instead of detecting mental impairment of the user 12, the neurofeedback system trains a user (as a driver) 12 to optimize concentration on the road and provide awareness to the user 12. The display device 20 displays a driving scenario 60 to the user 12, including a road 62 and a speedometer gauge 64, as illustrated in FIG. 9. The driving simulation system may utilize the communications device 22 illustrated in FIG. 6 to instruct the user 12 to focus on the road 62 and concentrate on driving steady at a specified posted speed limit.

The non-invasive driving simulation system may utilize the non-invasive brain interface assembly 14 to detect brain activity in the DLPFC of the user 12, and the computer 26 and/or database, server, or cloud structure 28 may extract features from the detected brain activity correlated to the concentration of the user 12 on the road 62 and maintaining the car steady at the specified speed limit while viewing the speedometer gauge 64. The end goal of the driving simulation system is to optimize the brain activity of the user 12 towards concentrating on the road 62 and maintaining the car steady at the specified speed limit. The computer 26 may update the speedometer gauge 64 based on the detected brain activity. If the brain interface assembly 14 is magnetically-based, the speedometer gauge 64 may be updated based on the beta power or the ratio of theta to alpha power of the detected brain activity. If the brain interface assembly 14 is optically-based, the speedometer gauge 64 may be updated based on contrast between the average time-of-flight (TOF) distribution collected across an entire session and average TOF distributions collected during concentration on the task.

As another alternative embodiment, a non-invasive attention/distraction prediction system may be similar to the non-invasive mental impairment detection system 10 described above, with the exception of, instead of detecting mental impairment of the user 12, the attention/distraction prediction system assesses the attentional state of the user 12 (e.g., a driver) and determines if the user 12 is fully engaged with driving or is inattentive.

Figure 10:
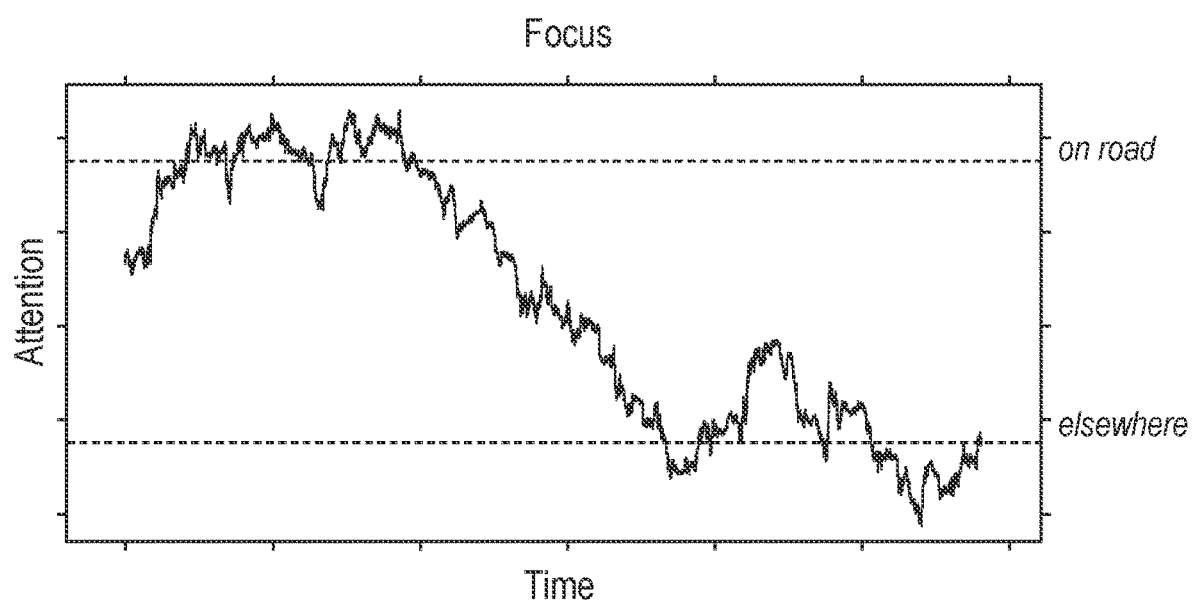
FIG. 10 is a diagram of an amplitude of brain activity detected by a non-invasive attention/distraction prediction system as a function of attention of a user on a road.

The attention/distraction prediction system may utilize the non-invasive brain interface assembly 14 to detect brain activity in the pre-motor cortex and/or DLPFC of the user 12, and the computer 26 and/or database, server, or cloud structure 28 may extract features from the detected brain activity correlated to concentration and the level of mental workload that is effecting that concentration, and predict whether the user 12 is going to shift his or her spatial attention. This can be reflected in the power spectrum of certain oscillatory bands or be analyzed via feeding time-frequency signals into neural network machines that predict correlates to level of concentration, as illustrated in FIG. 10. This level can then be monitored to assess driver awareness and correct focus to the road if workload is becoming saturated. The power spectrum of theta and alpha rhythms of the detected brain activity can be monitored across time to track drowsiness and used to create predictions prior to actual drowsiness or shifts to an inattentive state. The attention/distraction prediction system may optionally utilize the camera 24 to track the eyes of the user 12, such that the gaze position of the user 12 can be extracted and utilized in conjunction with the features extracted from the detected brain activity to predict if this upcoming shift of spatial attention is going to be off of the road.

Based on this information, the attention/distraction prediction system alerts the user 12. For example, if the attention/distraction prediction system determines that the user 12 is likely to shift his or her focus of the road, it can sound an alarm alerting the user 12 to focus on the road, or alternatively, may present a visual alert at the location of the attention focus predicted from the neural and eye tracking signals in order to minimize the obtrusiveness of an auditory alarm.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A mental impairment detection system, comprising:
   a sensory stimulation device configured for administering a sustained attention test to a user;
   a non-invasive brain interface assembly configured for detecting brain activity in a frontal lobe of the user while the sustained attention test is administered to the user; and
   at least one processor configured for determining a level of temporary mental impairment of the user by quantifying results of the sustained attention test administered to the user based on the brain activity detected in the frontal lobe of the user and comparing the quantified results of the sustained attention test administered to the user to baseline quantified results of the sustained attention test administered to the user when the user is known to not be mentally impaired.

2. The mental impairment detection system of claim 1, wherein the non-invasive brain interface assembly is configured for detecting the brain activity in a dorsolateral prefrontal cortex of the frontal lobe of the user.

3. The mental impairment detection system of claim 1, wherein the sensory stimulation device comprises a display device configured for displaying the sustained attention test to the user.

4. The mental impairment detection system of claim 3, wherein the sustained attention test comprises a psychomotor vigilance task.

5. The mental impairment detection system of claim 4, wherein displaying the sustained attention test comprises randomly or pseudo-randomly presenting a visual stimulus every few seconds over a period of time.

6. The mental impairment detection system of claim 5, further comprising a communication device configured for instructing the user to perform an action in response to each stimulus.

7. The mental impairment detection system of claim 3, wherein the sustained attention test comprises go/no-go tasks.

8. The mental impairment detection system of claim 4, wherein displaying the sustained attention test comprises randomly or pseudo-randomly presenting different types of stimuli one-at-a-time.

9. The mental impairment detection system of claim 8, further comprising a communication device configured for instructing the user to perform an action if one type of stimulus is presented to the user, and to not perform the action if another different type of stimulus is presented to the user.

10. The mental impairment detection system of claim 1, further comprising a camera configured for tracking head movements of the user, wherein the at least one processor is configured for determining the level of impairment of the user further based on the tracked head movements of the user.

11. The mental impairment detection system of claim 1, wherein the sensor stimulation device is further configured for administering a reflex test to the user, wherein the non-invasive brain interface assembly is further configured for detecting brain activity in a non-frontal lobe of the user while the reflex test is administered to the user, and the at least one processor is configured for determining the level of impairment of the user further based on the brain activity detected in the non-frontal lobe of the user.

12. The mental impairment detection system of claim 1, wherein the non-invasive brain interface assembly is one of an optical measurement assembly and a magnetic measurement assembly.

13. The mental impairment detection system of claim 1, wherein the non-invasive brain interface assembly comprises at least one sensor configured for detecting energy from a brain of the user, and processing circuitry configured for identifying the brain activity in response to detecting the energy from the brain of the user.

14. The mental impairment detection system of claim 13 wherein the non-invasive brain interface assembly comprises a head-worn unit carrying the at least one sensor.

15. The mental impairment detection system of claim 1, wherein the non-invasive brain interface assembly comprises a computer containing the at least one processor.

16. A non-invasive method of detecting mental impairment of a user, comprising:
   administering a sustained attention test to the user;
   non-invasively detecting brain activity in a frontal lobe of the user while the sustained attention test is administered to the user; and
   determining a level of temporary mental impairment of the user by quantifying results of the sustained attention test administered to the user based on the brain activity detected in the frontal lobe of the user and comparing the quantified results of the sustained attention test administered to the user to baseline quantified results of the sustained attention test administered to the user when the user is known to not be mentally impaired.

17. The non-invasive method of claim 16, wherein the brain activity is detected in a dorsolateral prefrontal cortex of the frontal lobe of the user.

18. The non-invasive method of claim 16, wherein administering the sustained attention test to the user comprises displaying the sustained attention test to the user.

19. The non-invasive method of claim 18, wherein the sustained attention test comprises a psychomotor vigilance task.

20. The non-invasive method of claim 19, wherein displaying the sustained attention test comprises randomly or pseudo-randomly presenting a visual stimulus every, few seconds over a period of time.

21. The non-invasive method of claim 19, further comprising instructing the user to perform an action in response to each stimulus.

22. The non-invasive method of claim 19, wherein the sustained attention test comprises go/no-go tasks.

23. The non-invasive method of claim 22, wherein displaying the sustained attention test comprises randomly or pseudo-randomly presenting different types of stimuli one-at-a-time.

24. The non-invasive method of claim 23, further comprising instructing the user to perform an action if one type of stimulus is presented to the user, and to not perform the action if another different type of stimulus is presented to the user.

25. The non-invasive method of claim 16, further comprising tracking head movements of the user, wherein the level of impairment of the user is further based on the tracked head movements of the user.

26. The non-invasive method of claim 16, further comprising:
   administering a reflex test to the user; and
   detecting brain activity in a non-frontal lobe of the user while the reflex test is administered to the user;
   wherein the level of impairment of the user is determined further based on the brain activity detected in the non-frontal lobe of the user.

27. The non-invasive method of claim 16, wherein detecting the brain activity of the user comprises one of optically detecting the brain activity of the user and magnetically detecting the brain activity of the user.

\* \* \* \* \*